(12) United States Patent
Tal

(10) Patent No.: US 10,463,388 B2
(45) Date of Patent: Nov. 5, 2019

(54) WIRE AND DEVICE FOR VASCULAR TREATMENT

(71) Applicant: Merit Medical Systems, Inc., South Jordan, UT (US)

(72) Inventor: Michael G. Tal, Woodbridge, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 116 days.

(21) Appl. No.: 14/947,256

(22) Filed: Nov. 20, 2015

(65) Prior Publication Data

US 2016/0338728 A1 Nov. 24, 2016

Related U.S. Application Data

(60) Continuation of application No. 12/950,488, filed on Nov. 19, 2010, now abandoned, which is a division of
(Continued)

(51) Int. Cl.
*A61B 17/3207* (2006.01)
*A61B 17/00* (2006.01)
*A61B 17/22* (2006.01)

(52) U.S. Cl.
CPC ............ *A61B 17/320758* (2013.01); *A61B 17/00008* (2013.01); *A61B 2017/0046* (2013.01);
(Continued)

(58) Field of Classification Search
CPC ...... A61B 17/320758; A61B 17/00008; A61B 17/32003; A61B 2017/22038; A61B 2017/22039; A61B 2017/22041; A61B 2017/2017; A61B 2017/22042; A61B 2017/32073; A61B 2017/320032; A61M 25/09; A61M 2025/09058; A61M 2025/09083; A61M 2025/02173; A61M 2025/09175
(Continued)

(56) References Cited

U.S. PATENT DOCUMENTS 2,212,477 A 8/1940 Mayer
3,405,712 A 10/1968 Pierick
(Continued)

FOREIGN PATENT DOCUMENTS

CA 2405273 10/2001
CN 2148536 12/1993
(Continued)

OTHER PUBLICATIONS

International Patent Application No. PCT/US2007/078367: International Search Report dated Jan. 11, 2008, 2 pages.
(Continued)

*Primary Examiner* — Kathleen S Holwerda
(74) *Attorney, Agent, or Firm* — Stoel Rives LLP

(57) ABSTRACT

A wire for use with a vascular treatment device may have a proximal end, a distal end, and a main shaft extending therebetween. The distal end may have a distal free end and a first segment. The first segment may extend from the main shaft and may be biased to a first included angle that is defined between the main shaft and the first segment and less than 180 degrees.

12 Claims, 31 Drawing Sheets

Related U.S. Application Data application No. 12/438,314, filed as application No. PCT/US2007/078367 on Sep. 13, 2007, now Pat. No. 7,967,834.

(60) Provisional application No. 60/916,110, filed on May 4, 2007, provisional application No. 60/825,529, filed on Sep. 13, 2006.

(52) U.S. Cl.
CPC ........... *A61B 2017/00398* (2013.01); *A61B 2017/00477* (2013.01); *A61B 2017/00778* (2013.01); *A61B 2017/22084* (2013.01)

(58) Field of Classification Search
USPC ................................................ 606/169, 180
See application file for complete search history.

(56) References Cited

U.S. PATENT DOCUMENTS

| | | |
|---|---|---|
| 3,530,492 A | 9/1970 | Ferber |
| 3,633,566 A | 1/1972 | Grabhorn |
| 4,278,085 A | 7/1981 | Shim |
| 4,403,611 A | 9/1983 | Babbit |
| 4,577,514 A | 3/1986 | Bradley |
| 4,586,921 A | 5/1986 | Berson |
| 4,854,325 A | 8/1989 | Stevens |
| 4,857,046 A | 8/1989 | Stevens et al. |
| 4,867,156 A | 9/1989 | Stack et al. |
| 4,876,109 A | 10/1989 | Mayer et al. |
| 4,906,236 A | 3/1990 | Alberts et al. |
| 4,936,845 A | 6/1990 | Stevens |
| 5,022,399 A | 6/1991 | Biegeleisen |
| 5,026,384 A * | 6/1991 | Farr ............... A61B 17/320758 606/159 |
| 5,047,013 A | 9/1991 | Rossdeutscher |
| 5,087,244 A | 2/1992 | Wolinsky et al. |
| 5,087,265 A | 2/1992 | Summers |
| 5,100,425 A | 3/1992 | Fischell et al. |
| 5,116,352 A * | 5/1992 | Schnepp-Pesch ........................... A61B 17/320758 604/22 |
| 5,135,517 A | 8/1992 | McCoy |
| 5,176,646 A | 1/1993 | Kuroda |
| 5,269,794 A | 12/1993 | Rexroth |
| 5,304,115 A * | 4/1994 | Pflueger ........... A61B 17/22012 604/22 |
| 5,330,481 A | 7/1994 | Hood |
| 5,350,390 A | 9/1994 | Sher |
| 5,356,418 A * | 10/1994 | Shturman ...... A61B 17/320758 606/159 |
| 5,358,507 A | 10/1994 | Daily |
| 5,415,636 A | 5/1995 | Forman |
| 5,449,351 A | 9/1995 | Zohmann |
| 5,514,151 A | 5/1996 | Fogarty et al. |
| 5,611,357 A | 3/1997 | Suval |
| 5,628,730 A | 5/1997 | Shapland et al. |
| 5,632,755 A | 5/1997 | Nordgen et al. |
| 5,675,228 A | 10/1997 | O'Bryan |
| 5,707,355 A | 1/1998 | Zimmon |
| 5,709,657 A | 1/1998 | Zimmon |
| 5,716,366 A | 2/1998 | Yates |
| 5,766,191 A | 6/1998 | Trerotola |
| 5,776,153 A | 7/1998 | Rees |
| 5,836,905 A | 11/1998 | Lemelson et al. |
| 5,893,858 A | 4/1999 | Spitz |
| 5,902,266 A | 5/1999 | Leone et al. |
| 5,908,395 A | 6/1999 | Stalker |
| 5,911,700 A | 6/1999 | Mozsary et al. |
| 5,976,164 A | 11/1999 | Bencini et al. |
| 6,048,332 A | 4/2000 | Duffy et al. |
| 6,090,118 A | 7/2000 | McGuckin, Jr. |
| 6,129,734 A | 10/2000 | Shturman et al. |
| 6,159,196 A | 12/2000 | Ruiz |
| 6,165,187 A | 12/2000 | Reger |
| 6,193,735 B1 | 2/2001 | Stevens |
| 6,193,736 B1 | 2/2001 | Webler |
| 6,231,518 B1 | 5/2001 | Grabek et al. |
| 6,261,272 B1 | 7/2001 | Gross |
| 6,273,882 B1 | 8/2001 | Whittier et al. |
| 6,290,675 B1 | 9/2001 | Vujanic et al. |
| D450,843 S | 11/2001 | McGuckin, Jr. et al. |
| 6,319,227 B1 | 11/2001 | Mansouri-Ruiz |
| 6,346,095 B1 | 2/2002 | Gross |
| 6,369,039 B1 | 4/2002 | Palasis et al. |
| 6,402,745 B1 | 6/2002 | Wilk |
| 6,443,929 B1 | 9/2002 | Kuracina |
| 6,482,215 B1 | 11/2002 | Shiber |
| 6,484,727 B1 | 11/2002 | Vaska et al. |
| 6,517,528 B1 | 2/2003 | Pantages et al. |
| 6,544,221 B1 | 4/2003 | Kokish et al. |
| 6,602,264 B1 | 8/2003 | McGuckin, Jr. |
| 6,645,221 B1 | 11/2003 | Richter |
| 6,673,025 B1 | 1/2004 | Richardson et al. |
| 6,679,886 B2 | 1/2004 | Weikel et al. |
| 6,824,550 B1 | 11/2004 | Noriega et al. |
| 6,824,551 B2 | 11/2004 | Trerotola |
| 6,852,118 B2 | 2/2005 | Shturman et al. |
| 6,939,313 B2 | 9/2005 | Saadat et al. |
| 7,025,774 B2 | 4/2006 | Freeman et al. |
| 7,048,695 B1 | 5/2006 | Schwager |
| 7,108,704 B2 | 9/2006 | Trerotola |
| 7,402,155 B2 | 7/2008 | Palasis |
| 7,419,482 B2 | 9/2008 | Nash |
| 7,670,328 B2 | 3/2010 | Miller |
| 7,713,231 B2 | 5/2010 | Wulfman |
| 7,862,575 B2 | 1/2011 | Tal |
| 8,029,491 B2 | 10/2011 | Aboul-Hosn et al. |
| 8,038,664 B2 | 10/2011 | Miller |
| 8,123,669 B2 | 2/2012 | Siess et al. |
| 2001/0004700 A1 | 6/2001 | Honeycutt et al. |
| 2002/0010418 A1 | 1/2002 | Lary et al. |
| 2002/0077594 A1 | 6/2002 | Chien et al. |
| 2002/0173812 A1 | 11/2002 | McGuckin et al. |
| 2002/0188276 A1 | 12/2002 | Evans et al. |
| 2003/0045860 A1 | 3/2003 | Leu |
| 2003/0120256 A1 | 6/2003 | Lary et al. |
| 2003/0225435 A1 | 12/2003 | Huter et al. |
| 2004/0092967 A1 | 5/2004 | Sancoff et al. |
| 2004/0147934 A1 | 7/2004 | Kiester |
| 2004/0220519 A1 | 11/2004 | Wulfman et al. |
| 2004/0254566 A1 | 12/2004 | Plicchi |
| 2005/0055040 A1 | 3/2005 | Tal |
| 2005/0055041 A1 | 3/2005 | Woods |
| 2005/0096642 A1 | 5/2005 | Appling |
| 2005/0165354 A1 | 7/2005 | Schwartz |
| 2006/0095015 A1 | 5/2006 | Hobbs |
| 2006/0106407 A1 | 5/2006 | McGuckin, Jr. et al. |
| 2006/0217692 A1 | 9/2006 | Neuberger |
| 2006/0224110 A1 | 10/2006 | Scott |
| 2006/0259052 A1 | 11/2006 | Pintor et al. |
| 2007/0112308 A1 | 5/2007 | Kay |
| 2007/0282359 A1 | 12/2007 | Tal |
| 2008/0009791 A1 | 1/2008 | Cohen |
| 2008/0108971 A1 | 5/2008 | Klein |
| 2008/0172012 A1 | 7/2008 | Hiniduma-Lokuge |
| 2008/0300571 A1 | 12/2008 | LePivert |
| 2009/0137906 A1 | 5/2009 | Maruyama |
| 2010/0125276 A1 | 5/2010 | Palermo |
| 2010/0268076 A1 | 10/2010 | Gat |

FOREIGN PATENT DOCUMENTS

| | | |
|---|---|---|
| CN | 1330913 A | 1/2002 |
| DE | 10059742 G | 6/2002 |
| DE | 10059742 | 8/2002 |
| EP | 0501081 | 9/1992 |
| EP | 1350473 | 10/2003 |
| EP | 2061385 | 6/2014 |
| FR | 2651682 | 3/1991 |
| JP | 2003/299662 | 10/2003 |
| JP | 2004508096 A | 3/2004 |
| JP | 2007-301392 A | 11/2007 |

(56) References Cited

FOREIGN PATENT DOCUMENTS

| | | |
|---|---|---|
| JP | 2008536554 A | 9/2008 |
| JP | 2009/078150 | 4/2009 |
| JP | 2009-254874 A | 11/2009 |
| WO | WO 98/012967 A1 | 4/1998 |
| WO | 1999047056 | 9/1999 |
| WO | WO 99/47056 | 9/1999 |
| WO | WO 00/07500 A1 | 2/2000 |
| WO | 0108561 A1 | 2/2001 |
| WO | WO 01/54754 | 8/2001 |
| WO | 2004112569 A2 | 12/2004 |
| WO | 2006055265 A1 | 5/2006 |
| WO | WO 2008/005888 A2 | 1/2008 |
| WO | 2010093630 A1 | 8/2010 |
| WO | 2010096717 A1 | 8/2010 |
| WO | 2010112618 A1 | 10/2010 |

OTHER PUBLICATIONS

International Patent Application No. PCT/US2007/078367: Written Opinion dated Jan. 11, 2008, 5 pages.
Williams et al., "Sclerosant Treatment of Varicose Veins and Deep Vein Thrombosis", Archives of Surgery, Nov. 1984, vol. 119, No. 11, 1283.
VenaSeal Closure System. Viewed online Mar. 1, 2019 at http://medtronicendovenous.com/patients/7-2-venaseal-closure-procedure/. Medtronic. Minneapolis, MN.
ScleroSafe. Viewed online Mar. 1, 2019 at http://www.vvtmed.com/products/sclerosafe/. VVT Medical. Kfar Sava, Israel.
V-Block System. Viewed online Mar. 1, 2019 at http://www.vvtmed.com/products/v-block/. VVT Medical. Kfar Sava, Israel.

\* cited by examiner

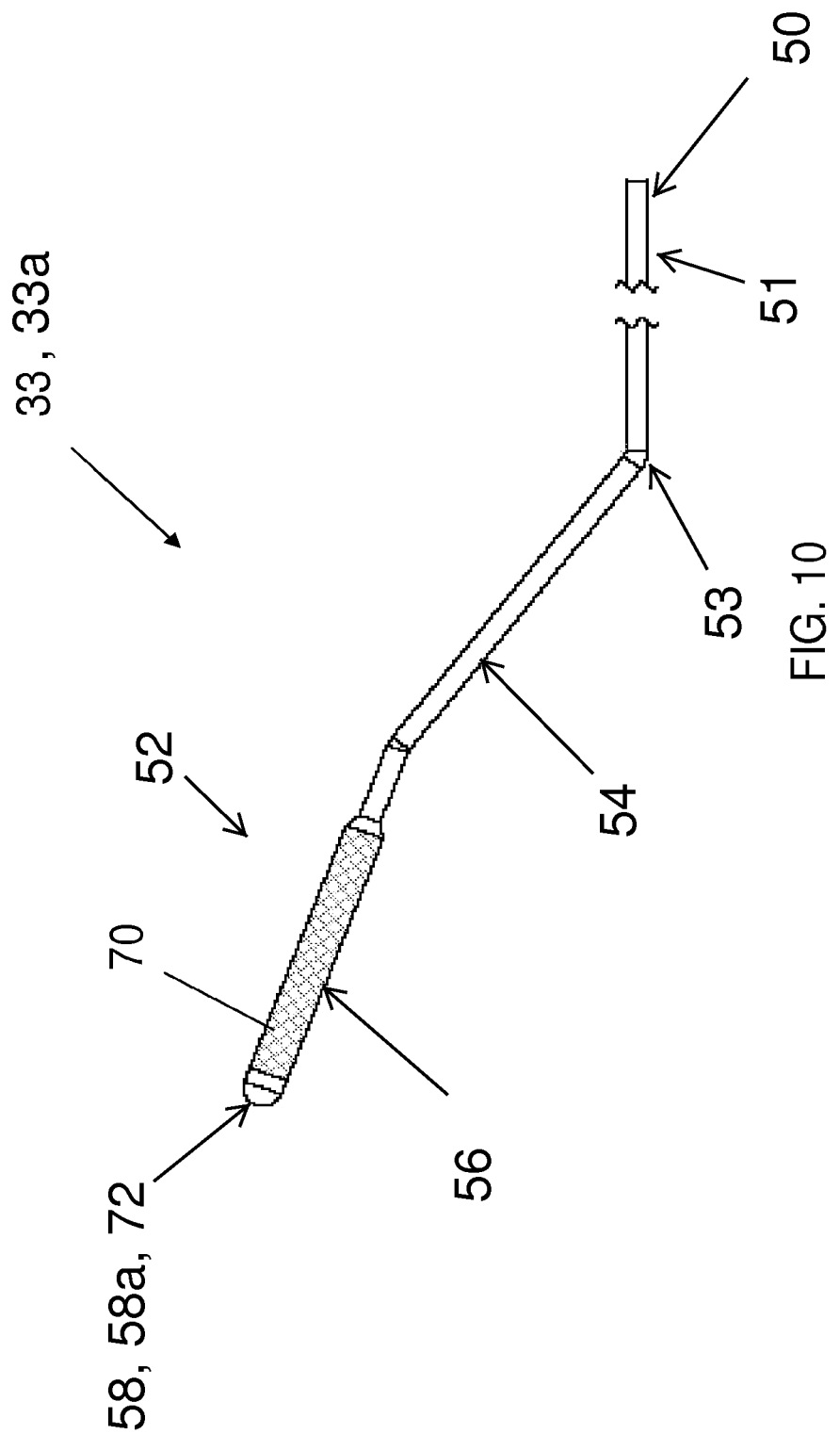

FIG. 14A

FIG. 16A

FIG. 17A

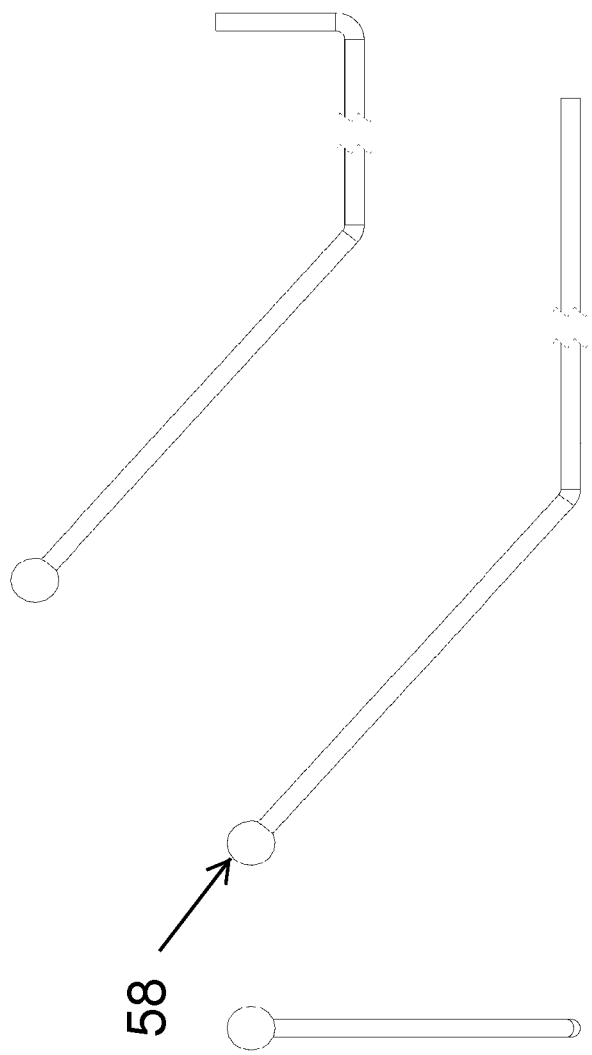

FIG. 18A

FIG. 19A

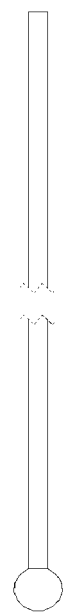
FIG. 20A

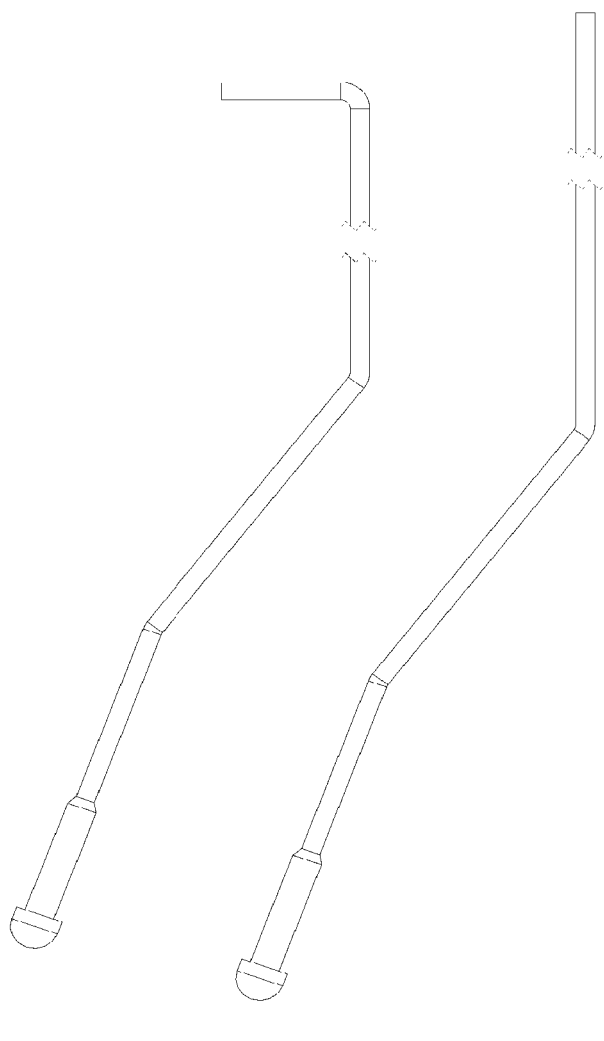
FIG. 21

FIG. 21A

58

WIRE AND DEVICE FOR VASCULAR TREATMENT

CROSS-REFERENCE TO RELATED APPLICATIONS

This application is a continuation of U.S. application Ser. No. 12/950,488, filed Nov. 19, 2010, which is a divisional of U.S. application Ser. No. 12/438,314 filed Feb. 20, 2009, which is the National Stage of International Application No. PCT/US2007/078367, filed Sep. 13, 2007, which claims the benefit of U.S. Provisional Application No. 60/825,529, filed Sep. 13, 2006, and U.S. Provisional Application No. 60/916,110, filed May 4, 2007, all of which are hereby incorporated herein by reference.

SUMMARY

A vascular treatment device may include (1) a handle having a motor, a trigger, and a male coupling, and (2) a cartridge, engageable to the handle, having a female coupling, a wire, and a sheath fixed to the cartridge. When the female coupling is not engaged to the male coupling, the sheath may cover the distal end of the wire, allowing safe advancement of the device into the patient's vasculature, and when the female coupling is engaged by the male coupling, the distal end of the wire may be exposed from the sheath and used.

BRIEF DESCRIPTION OF THE DRAWINGS

FIGS. 9-10 depict various embodiments of wire distal ends.

FIGS. 14-14A, 15-15A, 16-16A, 17-17A, 18-18A, 19-19A, 20-20A, 21-21A, 22-22A, 23, and 24 depict various embodiments of wire distal ends.

DETAILED DESCRIPTION

A vascular treatment device may be used for ablating blood vessels, such as varicose veins, and for treating thrombosis by macerating a clot and injecting a thrombolytic drug, among other uses. A vascular treatment device may include a rotatable wire, so sized and shaped for ablating blood vessels, coupled to a cartridge that is engageable to a handle. The wire may thus be indirectly engaged with a motor in the handle such that the wire rotates when the motor is turned on. When the device is used for treating a varicose vein, the rotating wire may perturb the vessel to cause vasospasm, a condition in which blood vessels spasm, and may cause damage to the vessel wall to promote sclerosis. During a thrombectomy procedure, the wire may macerate a clot without causing damage to the vessel wall.

Figure 1:
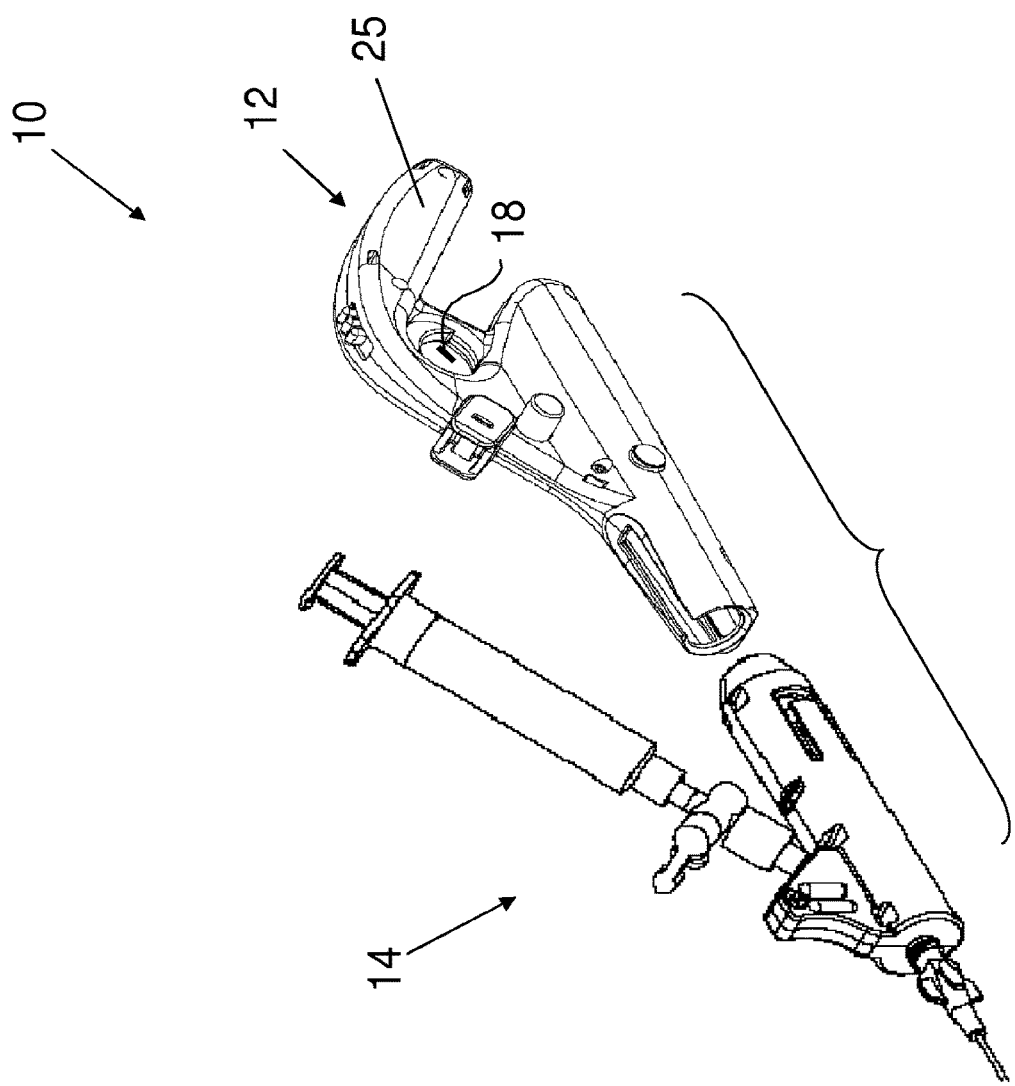
FIG. 1 shows an embodiment of an assembly of a vascular treatment device.
Figure 2:
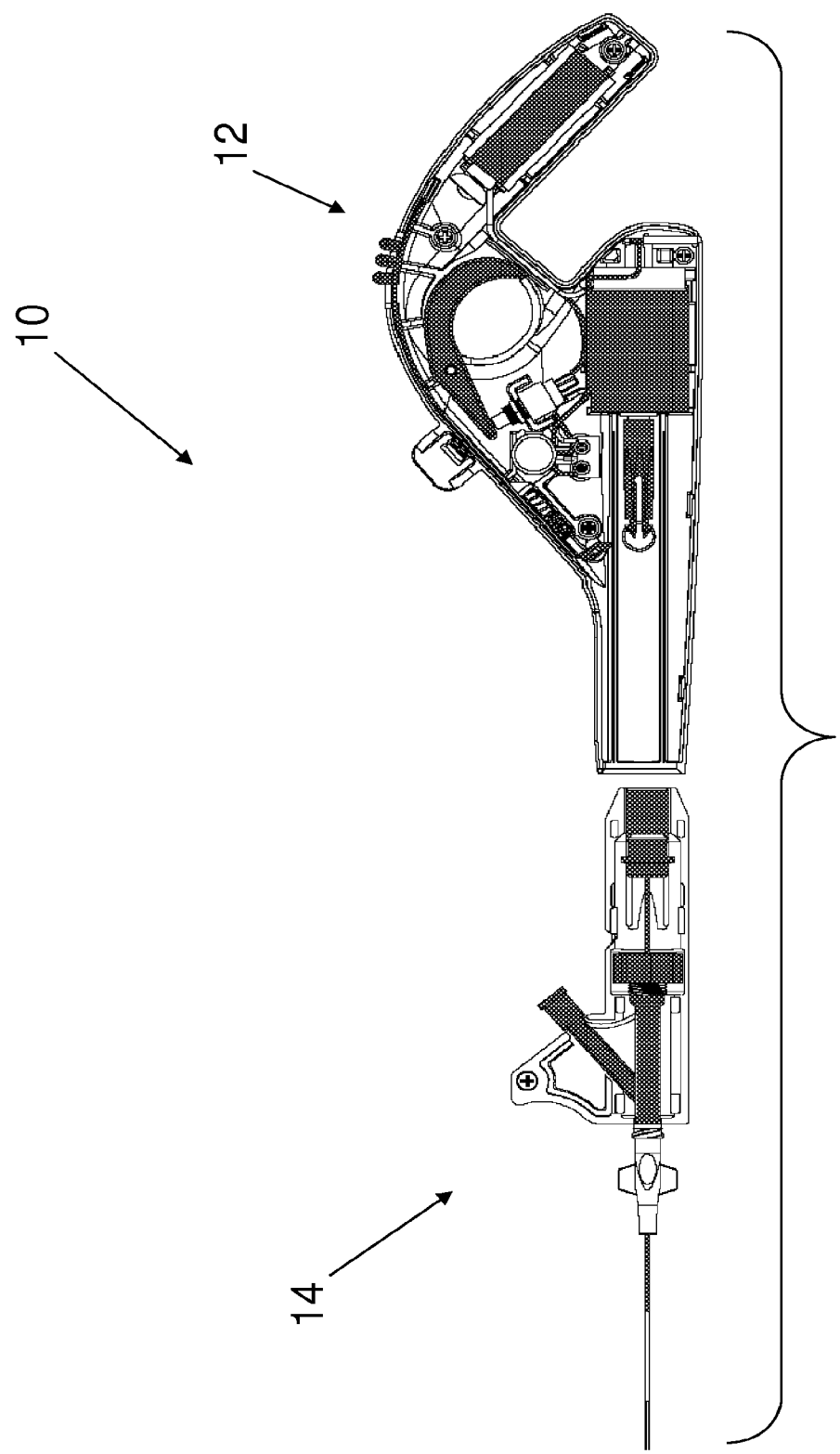
FIG. 2 illustrates a longitudinal cross-sectional view of the embodiment illustrated in FIG. 1.

FIG. 1 shows an embodiment of an assembly of a vascular treatment device 10 having a handle 12 and a cartridge 14. The cartridge 14 may be so sized and shaped to engage to the handle 12 by fitting one component to another as shown. An embodiment of the handle 12 is shown in greater detail in FIG. 3. The handle may define a receptacle 29 in which the male coupling 30 is positioned to receive the female coupling 40 of the cartridge 14 when the cartridge 14 and the handle 12 engage. The handle 12 may include a motor 22, a trigger 26, and a male coupling 30. The male coupling 30 may be connected to the motor 22 in such a way that the motor rotably drives the male coupling upon activation. A potentiometer 24 may be electrically coupled to the motor 22 to control a speed of the motor. The trigger 26 may be mounted on the handle and transitionable between a first state, which does not couple the motor to a power source electrically, and a second state, which couples the motor to a power source.

The handle 12 may also include a power source 20 and a microswitch 28 connected to the motor 22 by a wire 32. The microswitch 28 may be interposed in an electrical circuit connecting the trigger 26 and the motor 22. The microswitch may be biased to an open position such that the circuit between the trigger and the motor is open. When the cartridge 14 is engaged in the handle 12, the cartridge may press against the microswitch, causing it to transition to a closed state, thereby completing the electrical circuit connecting the trigger 26 and motor 22. For example, the microswitch may include two contacts with a conductor that is attached to one contact and disconnected from the second contact when the microswitch is in an open state. In one embodiment, the conductor may include a strip of metal that hangs in the channel into which the cartridge is slid during engagement with the handle. As the cartridge is engaged in the handle, it pushes the metal strip out of the channel and into connection with the second contact of the micro switch. One advantage gained from such configuration may be that a user will not be able to activate the device inadvertently by pressing on the trigger before he/she is ready to use the device, i.e., before the cartridge 14 is fully engaged to the handle 12.

Figure 3:
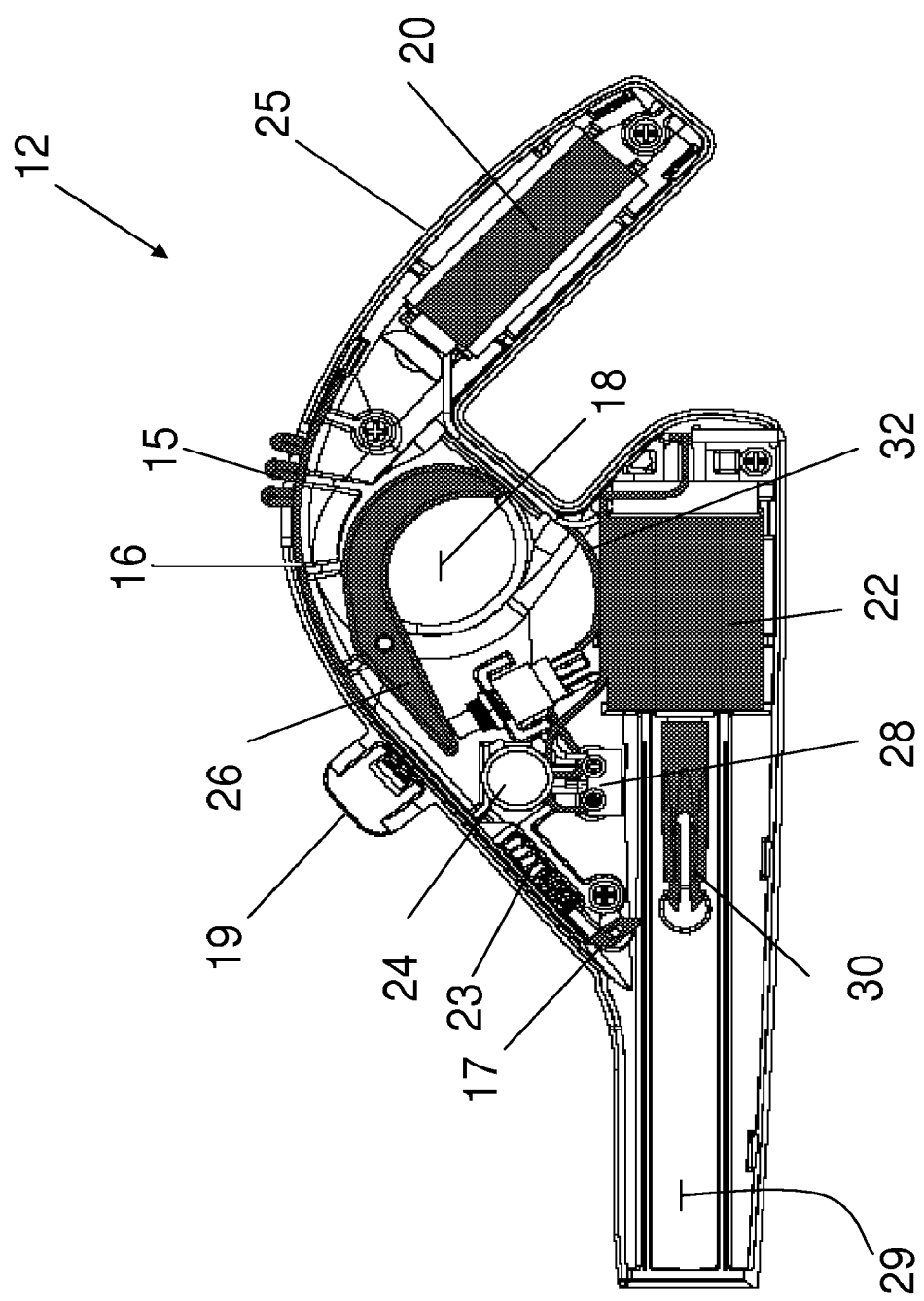
FIG. 3 shows a longitudinal cross-sectional view of a handle.

The handle may 12 also include a switch 16 as shown in FIG. 3. The switch 16 allows the cartridge 14 to be received by, and secured in, the handle 12. The switch may include a grip 15 to permit a user to operate the switch with a finger The switch may also include a gate 17 that alternately obstructs or locks the cartridge, depending on the gate's position. For example, a user may put a thumb on the grip 15 and push the switch 16 away from the handle grip 25 to transition the switch 16 from a first position, in which gate 17 is positioned in the channel and so prevents engagement of the cartridge 12 and the handle 14, to a second position in which gate 17 is moved out of the channel and thereby permits engagement of the cartridge and the handle. Upon release of the biased switch 16, the gate 17 may fit into a complementary detent in the cartridge and thereby help keep the cartridge engaged with the handle.

The gate 17 may be biased to the first position by a spring 23 contacting the handle. As the user pushes the switch 16 away from the handle grip 25, the switch 16 will push on the spring, thereby creating a restoring force to urge the switch to its original position once the user releases the switch.

As noted above, the gate 17 may be further transitionable to a third position which prevents disengagement of the cartridge 14 from the handle 12. For example, the gate 17 may be forced into the detent 35 (shown in FIG. 4), defined by the cartridge 14, when the biased switch 16 returns to its original position from the second position to lock the cartridge to the handle.

One or more portions of the handle 12 may define a trigger ring 18 in which the trigger is at least partly disposed and about which the handle is so arranged as to be balanced when supported from only one or more portions of the handle that define the trigger ring. In this manner, a user may balance the handle simply by supporting it with a single finger, such as an index finger, against a portion of the handle that defines the trigger ring 18. As motor 22 may well be the heaviest component in the handle, it can be positioned below the trigger 26 as shown in FIG. 3 to reduce the bending moment applied by the motor 22 on a finger supporting the handle by the trigger ring, thereby reducing fatigue experienced by the user.

The handle 12 may be formed by joining two outer casing pieces together.

Figure 4:
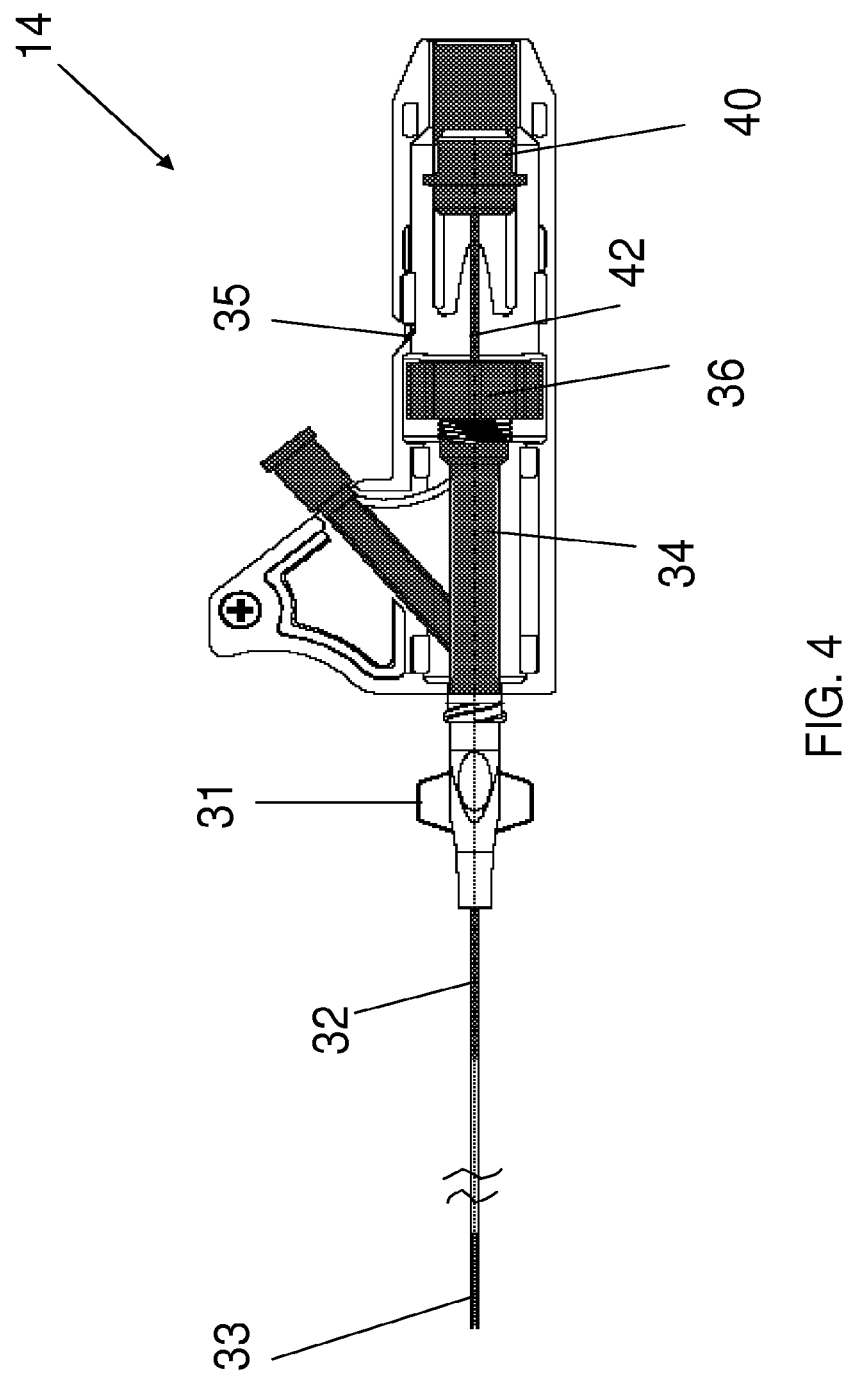
FIG. 4 illustrates a longitudinal cross-sectional view of a cartridge.

An embodiment of the cartridge 14 shown in FIG. 1 is illustrated in greater detail in FIG. 4. The cartridge 14 may include a female coupling 40, a wire 33 (shown as a broken line), and a sheath 32 fixed to and extending from the cartridge 14. The wire may be fixed to the female coupling 40; for example, the wire's proximal tip may be bent approximately 90 degrees to fit through a channel that is sized and shaped to receive the bent end of the wire. A setscrew may be received in the female coupling 40 and/or an appropriate adhesive may be used to secure the wire and prevent it from rotating with respect to the female coupling.

The sheath 32 may define a lumen through which the wire 33 runs. The sheath 32 may have a wide range of inner and outer diameters. In some embodiments, the sheath may have an inner diameter in the range of from 0.022 inches to 0.048 inches. In some embodiments, the sheath 32 may have an outer diameter in the range of from 0.025 inches to 0.051 inches. The outer diameter of the sheath may also be in the range that is consistent with the standard needles having corresponding inner diameters. For example, the sheath may be so sized and shaped to be insertable in a standard needle or vascular sheath having an inner diameter in the range of from 0.0035 inches to 0.1060 inches, or from 0.0160 inches to 0.0420 inches, or from 0.0420 inches to 0.0630 inches, or from 0.0115 inches to 0.0630inches. The maximum outer diameter of the sheath may be less than 0.035 inches to allow the sheath to be inserted through a intravenous needle or catheter having an inner diameter of less than 0.0039 inches to allow a wider range of practitioners to perform the procedure. Needles, catheters or vascular sheaths with an outer diameter greater than 0.079 inches (6 French, Fr) or 0.092 inches (7 Fr) typically require insertion to be performed by a vascular surgeon or interventional radiologist.

The sheath 32 may also include external markings at regular intervals which may guide the user to monitor the insertion or removal speed of the device 10.

Figure 5:
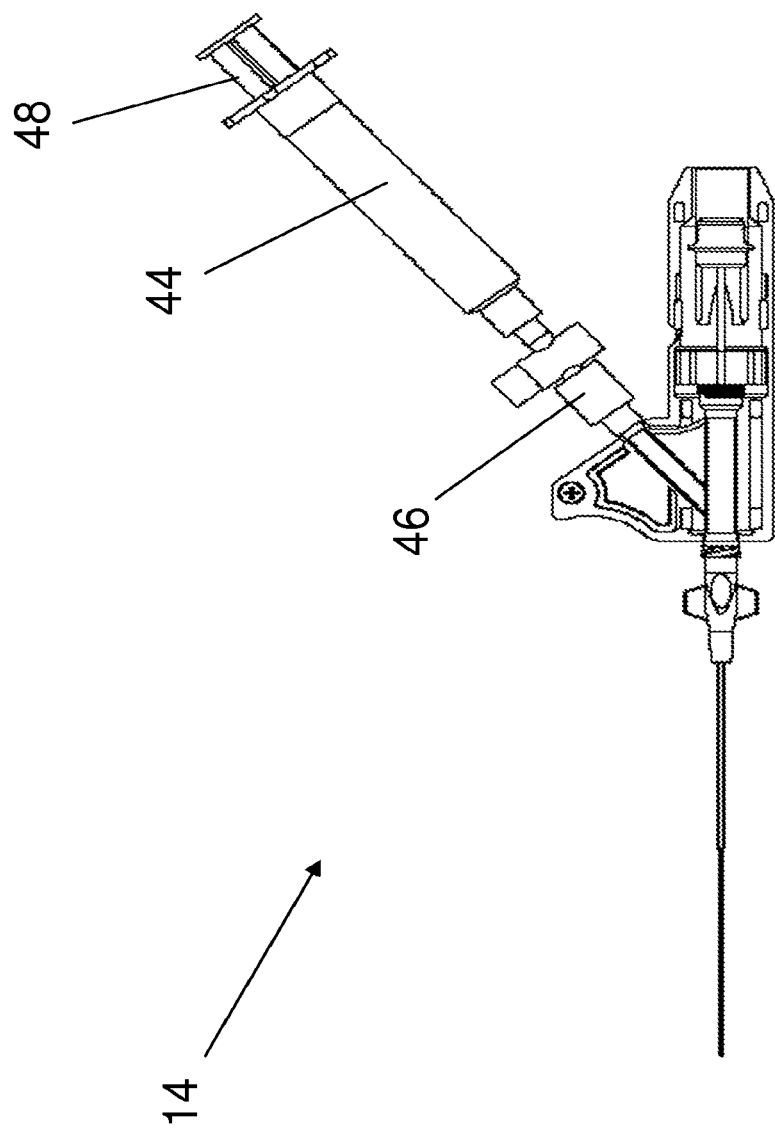
FIG. 5 shows the cartridge illustrated in FIG. 4 with a syringe and a stopcock attached.

One exemplary embodiment depicting a reservoir connectible to the cartridge may include a syringe 44, a stopcock 46, and a plunger 48 as shown in FIG. 5. The syringe 44 may be in fluid communication with the bore of the sheath 32 for releasing a substance at the wire distal end, such as a sclerosant (examples of which include polidocanol, sodium tetradecyl sulfate, and hypertonic saline), or thrombolytic drug (examples of which include alteplase (Activase), anistreplase (Eminase), streptokinase (Streptase, Kabikinase), urokinase (Abbokinase), and tissue plasminogen activator (TPA). In this manner, physical perturbation by the wire may be synergistically combined with drug treatment to improve device efficacy.

The handle 12 may include a support 19 (shown in FIG. 3) so positioned as to receive the syringe 44. The support 19 may be so sized and shaped to be compatible with the standard syringes and may prevent the syringe from falling out during injection, especially if the material being injected has high volume and/or viscosity and requires significant user thumb pressure upon the syringe. When the cartridge 14 with an attached syringe 44 is engaged to the handle, the syringe 44 may snap onto the support 19. As shown in FIG. 1, the support may be formed from two brackets which cradle the syringe. An alternative embodiment shown in FIGS. 6 and 7 includes a support formed from a single hook that wraps partially around the syringe. These embodiments allow use of the device with the right as well as left hand, depending on the user's preference and/or the patient's position on the treatment table.

The handle 12 and the syringe 44 may be so sized, shaped, and positioned as to permit a user to actuate the trigger 26 with the index finger of a hand and simultaneously depress a plunger 48 into the syringe with the thumb of the same hand, allowing a treatment drug to be deployed from the syringe through the sheath while the wire 33 is rotating. For example, a user may hold the handle by positioning the handle grip 25 in the center of the palm and wrapping third, fourth, and fifth finger around the handle grip and putting an index finger through the trigger ring 18 and if needed, placing a thumb to depress the plunger to release treatment drug into the syringe. The handle may be so designed to allow both rightand left-handed users to operate.

The stopcock 46 shown in FIG. 5 may allow reloading of fluid and also changing the fluid concentration of composition as well as mixing of the sclerosant fluid with gas. For example, air can be mixed for generating foam as well as agitating existing sclerosant/gas mixture and also recreating the foam, because the foam has a limited duration (typically a minute or less) before the fluid and gas start to separate. The stopcock 46 may allow the fluid composition mixture to be agitated without disconnecting the syringe from the cartridge or without stopping the procedure.

A standard Y hemostasis connector 34 as shown in FIG. 4, or other Y hemostasis connector, may be used to aid in fluid communication between the syringe 44 and the lumen defined by the sheath 32. A Y– hemostasis connector 34 may be connected to the female luer hub 31 and to the tubing nut 36 to prevent the fluid from leaking into the region containing the motor 22. An 0-ring may be used to prevent leaks around the wire shaft. Wire tubing 42 may be so sized and shaped to receive the wire 33 and attached to the female coupling 40. Combining the above mentioned components may allow the motor to rotate the wire without increasing the torque beyond the appropriate working range. The motor may spin in the range of from 500 to 3000 rpm-4000 rpm for varicose vein destruction and thrombectomy procedures. The handle may also include a built-in RPM display for user to read the speed or may include an electrical port through which the speed may measured by an external monitor.

The male coupling 30 on the handle 12 may be biased toward an expanded state and transitionable from the expanded state to a contracted state. The female coupling 40 may be so sized and shaped as to transition the male coupling 30 from the expanded state to the contracted state during engagement of the handle 12 and the cartridge 14. As the male coupling 30 and the female coupling 40 fully engage each other, the male coupling displaces the female coupling detents to allow the female coupling to slide within the cartridge.

Attaching the female coupling 40 to the male coupling 30 thereby causes the sheath 32 to slide back relative to the wire. This occurs because the sheath is fixed to the cartridge, while the wire is fixed to the female coupling. As the cartridge is fully seated in the handle, the female coupling is pushed forward in the cartridge. So when the female coupling 40 is not engaged by the male coupling 30, the sheath 32 may cover the distal end of the wire 33, allowing it to be safely advanced in the patient's vasculature; and when the female coupling 40 is engaged by the male coupling 30, the sheath may reveal the distal end of the wire. Consequently, when the female and male couplings are engaged the distal tip of the wire is revealed, and (2) the wire is operably coupled to the motor 22 through the female and male couplings, to allow the motor to rotate the wire 33. As noted above, the cartridge may also trip a lever arm coupled to the microswitch 28 to complete a circuit between the trigger 26 and the motor 22. The male coupling 30 may be so sized and shaped as to return to the expanded state once the cartridge 14 and the handle 12 are fully engaged as described earlier.

The female coupling may be disengaged from the male coupling to re-cover the distal tip of the wire when the wire is to be removed for the site of use, or if a treatment is interrupted. Disengaging the female coupling from the male coupling slides the wire 33 with respect to the sheath 32 (attached to the cartridge fixed to the handle); as a result the tip of the wire is no longer exposed, allowing it to be safely removed. This mechanism may protect the tip of the wire 33 prior to use and also protect the blood vessels and other body tissues during removal or repositioning of the device.

The male coupling 30 may have at least two prongs separated by slitted portions to facilitate the transition from the expanded state to the contracted state. The male coupling may be made with polycarbonate, plastic, or other materials which allow transitioning between an expanded state to a contracted state.

In some embodiments, the vascular treatment device 10 may be of a single piece construct having a handle and a cartridge. The cartridge may be assembled to the handle during manufacturing and be able to transition within the handle between a first position, where the male and female couplings are not engaged, and a second position, where the male and female couplings are engaged. An embodiment of such device may allow the cartridge to slide back and forth within a predetermined range, such as the first and the second position, in the groove defined by the handle, but the cartridge may not disengage itself from the handle. A sheath may be fixed and extend from the cartridge and define a lumen through which the wire runs. The cartridge may also include a syringe to be received by a support mounted on the handle.

In this embodiment, the handle may include a motor, a motor coupling, a trigger, and a power source. The wire having a main shaft, a distal end, and a proximal end which is fixed to the motor coupling may be attached to the motor coupling. The motor coupling may be rotably driven by the motor. The trigger may be mounted on the handle and be transitionable between a first state, which does not couple the motor to a power source electrically, and a second state, which couples the motor to a power source. The handle may also include a microswitch to permit trigger and the motor to be electrically coupled to one another.

At the first position, the cartridge may cover the distal tip of the wire. At the second position, the cartridge (1) exposes the distal tip of the wire from the sheath, and (2) completes a circuit between the trigger and the motor by tripping a lever arm coupled to the microswitch. Therefore, the single piece construct vascular treatment device may allow a user to obtain similar functionality as the device explained earlier and shown in FIG. 1.

Figure 6:
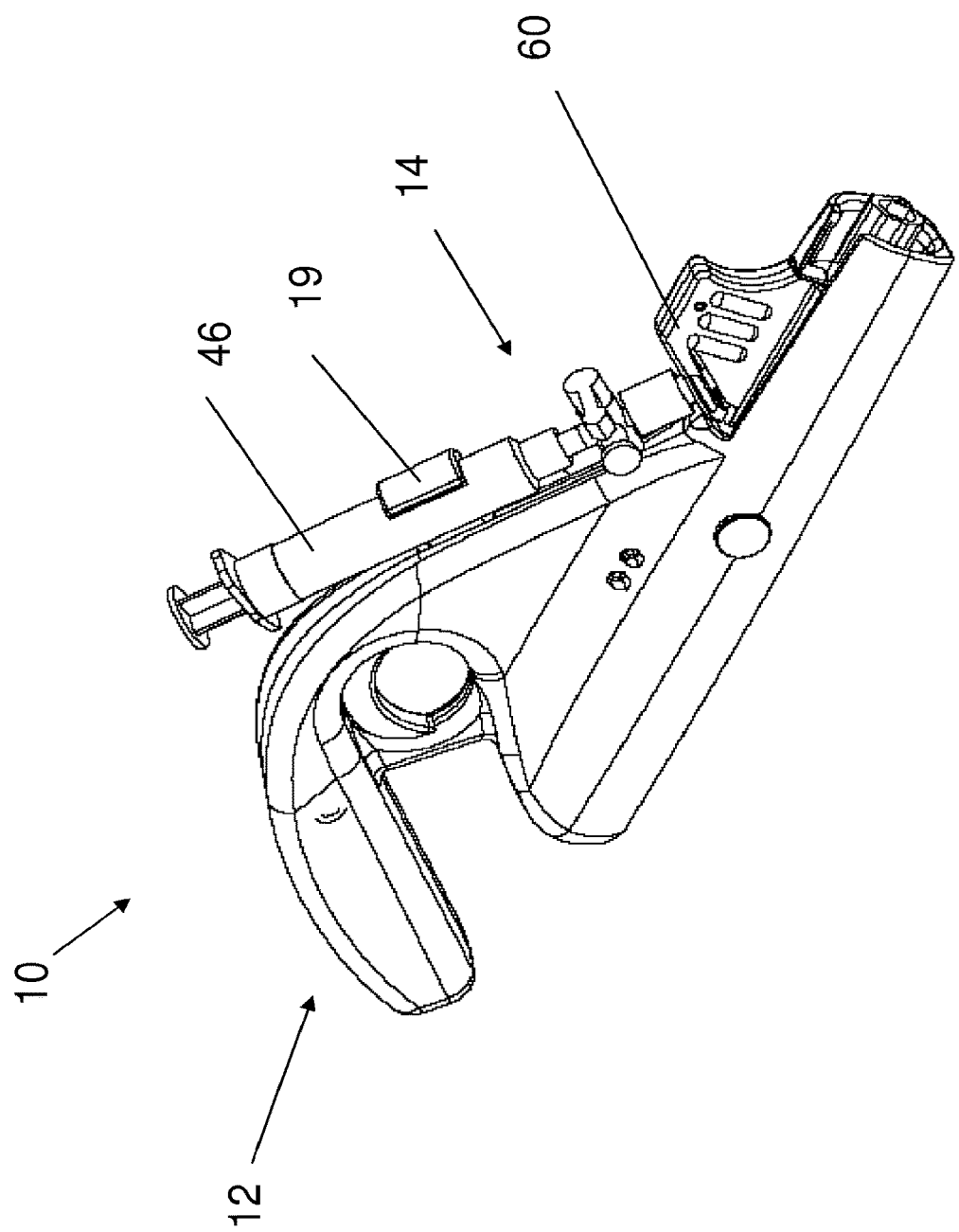
FIG. 6 shows a perspective view of an embodiment of a vascular treatment device having a single syringe support.
Figure 7:
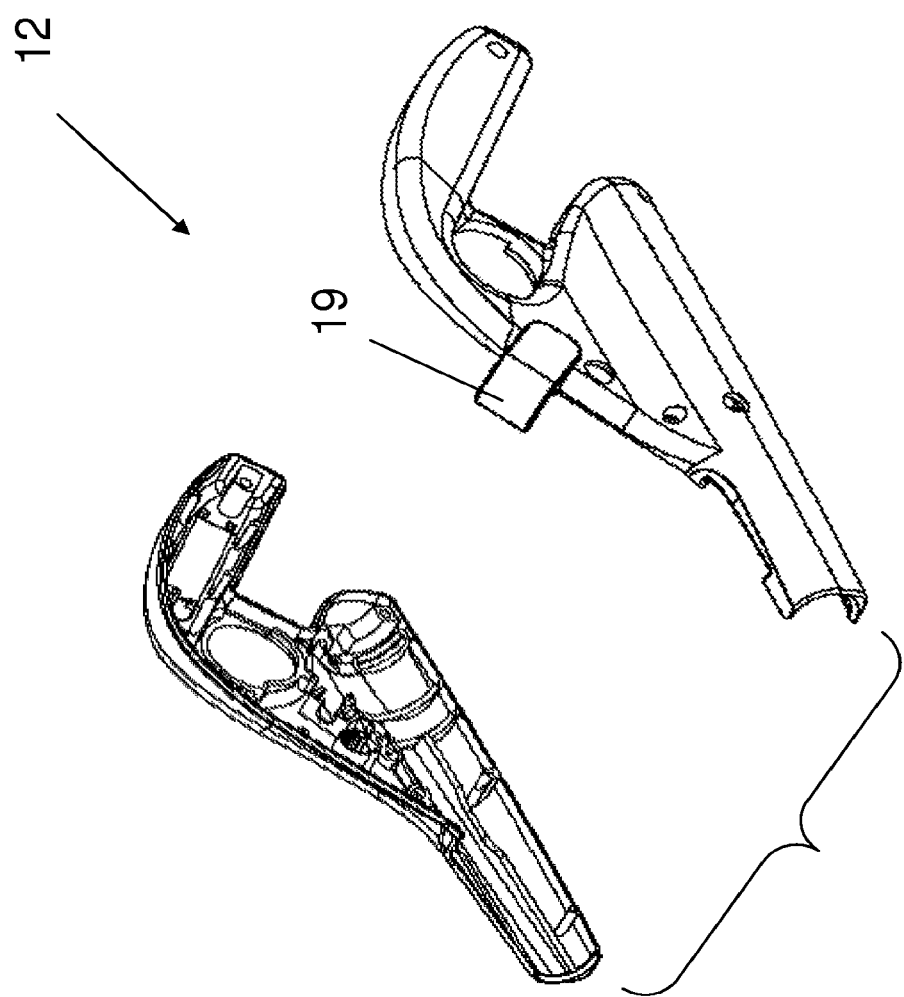
FIG. 7 illustrates an exemplary assembly of the handle of the embodiment depicted in FIG. 5.

FIG. 6 illustrates another embodiment of vascular treatment device 10. The handle may have a support 19 for the syringe 46 in the form of a hook, as described above. This embodiment may be assembled by mating two casings as shown in FIG. 7. The syringe may snap onto the support and remain in position during the use of the device. The support 19 (and/or handle 12) may be made of SLA resin or other materials that would allow the support to withstand the snapping force applied by the syringe.

Figure 8:
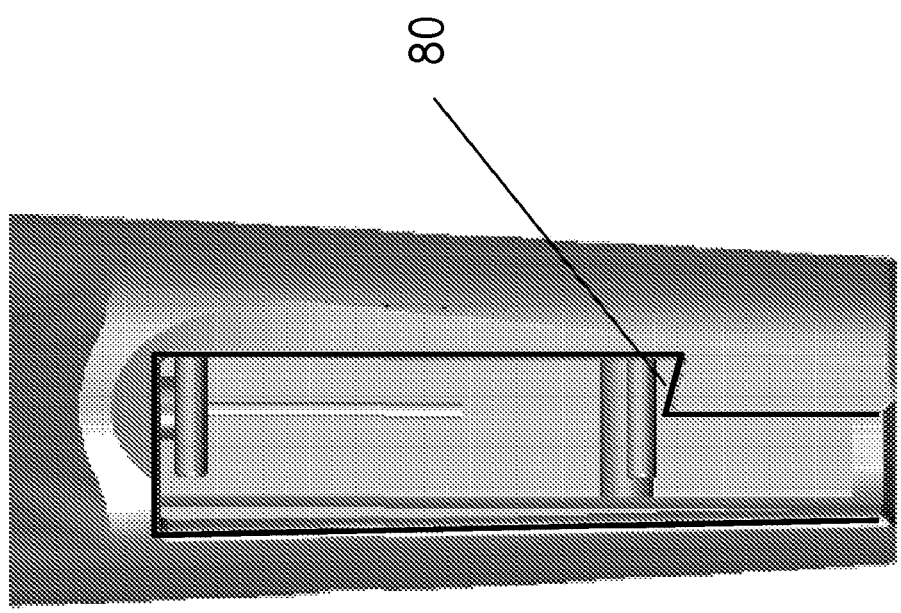
FIG. 8 depicts a top plan view of a portion of the handle illustrated in FIG. 7.

FIG. 8 shows a top view of the end of an alternate embodiment of handle 12 having a notch 80 for retaining the cartridge 14 (not shown) to the handle 12. In the previously mentioned embodiments, the handle had a switch that may be coupled to a gate which held the cartridge to the handle. In this configuration, the notch 80 may prevent the cartridge from disengaging from the handle. In use, a user may slide the cartridge into the handle and then "cock" the cartridge into notch 80 to prevent the cartridge from slipping out of the handle.

A wide variety of distal wire tips may be used; FIGS. 9-11, 14-14A, 15-15A, 16-16A, 17-17A, 18-18A, 19-19A, 20-20A, 21-21A, 22-22A, 23, and 24 show several examples.

Figure 9:
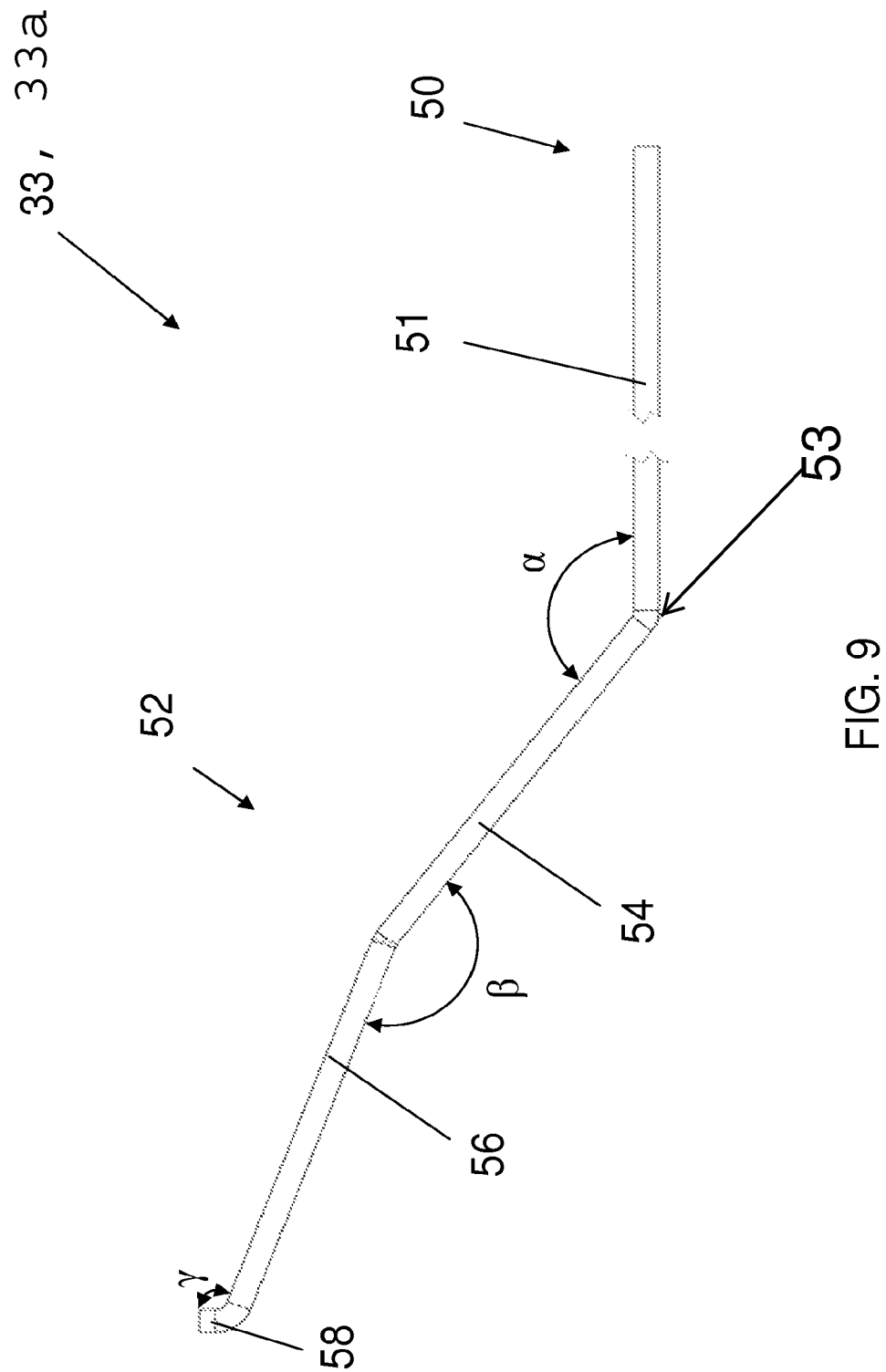

FIG. 9 shows an embodiment of a wire 33 having a shaft 33a that has a proximal end 50, a distal end 58, and in proximal-to-distal order, a first segment 51 and a second segment 52. The first segment 51 may extend between the proximal end 50 and a bend 53. The second segment 52 and may be biased in relation to the first segment 51 to a first included angle $\alpha$ that is less than 180 degrees. The second segment 52 includes a first portion 54, a second portion 56, and the third portion 58a. First portion 54 and second portion 56 may be biased to a second included angle $\beta$ that is less than 180 degrees. The third portion 58a may extend from the second portion 56 to distal end 58 such that second portion 56 and distal end 58 are biased in relation to each other at a third included angle y that is less than 180 degrees.

The second included angle $\beta$ may be greater than the first included angle $\alpha$. The sum of the first included angle $\alpha$ and the third included angle $\gamma$, minus the second included angle $\beta$, may be in the range of about 70 degrees to about 110 degrees. The sum of the first included angle $\alpha$ and the third included angle $\gamma$, minus the second included angle $\beta$ may be in the range about 80 degrees to about 100 degrees. The sum of the first included angle $\alpha$ and the third included angle $\gamma$, minus the second included angle $\beta$ may be about 90 degrees.

The third portion 58a of the shaft 33a may have a length that is smaller than the inner diameter of the sheath 32. For example, the portion 58a may have a length of less than 0.028 inches or it may have a length that is equal to or smaller than two-thirds of the inner diameter of the sheath 32.

The perpendicular distance measured from an center axis of the main shaft 51 to the free end may be less than 0.3 inches. The first portion 54 and the second portion 56 each may have a length in the range of about 0.2 inches to about 0.3 inches, or in the range about 0.24 inches to about 0.26 inches. The length of the first portion 54 may be in the range of about 0.248 inches to about 0.25 inches, and the length of the second portion is in the range of about 0.25 inches to about 0.252 inches. In one embodiment, the length of the first portion 54 may be 0.249 inches, and the length of the second segment is 0.2504 inches.

The distal end 58 of the wire 33 may include at least two linear segments oriented at a non-zero angle relative to one another. Having at least two linear segments may allow the distal tip of the wire to tuck into a sheath without touching the wall of the sheath, and it may also allow the main shaft of the wire to run along the vessel wall while the tip (for example, the third segment) of the wire digs into the vessel wall.

The distal end 58 may have a wide variety of configurations, depending on the intended use. The wire shape may be "atraumatic," meaning that it may be shaped such that insertion causes little or no spasm or damage to the vessel. For example, FIG. 10 shows a distal end 58 terminating with a hemispheric free end. The hemispheric end maybe textured or mechanically or chemically altered to create a roughened surface. Other atraumatic tips may include an end having a full radius, or a J-curved shape, or simply a curved shape.

FIG. 10 shows an atraumatic tip having a sleeve extending from the hemispheric shape along the wire 33 towards the proximal end of the wire. The sleeve 70 can add strength to the distal tip, thereby increasing the scrapping force and increasing the contact surface area to prevent detachment of the hemispheric tip 72.

In other embodiments, the distal tip 58 may be "aggressive" and be bent or curved so that it scrapes the vessel wall. FIG. 9 shows the distal end 58 having a flat free end with a sharp edge around. An aggressive distal tip 58 may also be created by beveling an edge to create a sharp point. The distal tip having a cutting blade, like a shark's fin, may also be aggressive. The distal tip 58 may be roughened to make the distal tip cut more aggressively and/or cause spasm to the blood vessel wall.

A roughened surface may be formed by subjecting an initially smooth steel to abrasion, machining, blasting, chemical etching such as acid etching (for example, nitric acid, hydrofluoric acid, hydrochloric acid, and/or sulfuric acid). A roughened outer surface may also be created by rolling a sheet metal, such as a sheet forming the sleeve 70, onto an irregularly shaped guide to create surface irregularity.

Also, the outer surfaces of the first, the second, and/or the third segments may be coated with an abrasive to roughen the surface. Other surface treatments may include a bastard cut file type or diamond grit. For example, 30 grit diamond may produce an aggressive surface and 200 grit diamond may produce a non-aggressive surface.

During use, especially with a roughened tip, the wire may be periodically re-encased in the sheath to help dislodge debris from the wire tip and keep the device operating normally.

An aggressive surface may also be formed on the first portion 54 and/or the second portion 56 of the wire 33 by introducing a screw threaded profile with a second wire along the length of the wire 33 by following a screw flights of various shapes such as a square, or a rhomboid, or a trapezoid, or a parallelogram, or an ellipse, or a triangle, or a pentagon.

FIG. 10 shows an embodiment having second portion 56 with a sleeve 70 having a roughened outer surface using one of various methods mentioned earlier. In addition to showing a roughened surface treatment, FIG. 10 further illustrates a wire with a weight added at the distal tip, in this case the weight is added by a sleeve with a roughed outer surface. The weight may be centered on the wire or eccentrically positioned. An eccentric weight may cause the wire to flail about during rotation. The flailing may perturb the vessels more aggressively compared to a wire with centrically added weight.

The distal end 58 of the wire 33 may also include a curved segment. The curvature of the curved segment may be constant, or it may follow other curves, such as a sector of an ellipse or an oval. The distal end 58 of the wire 33 may also have a straight segment distal to the curved segment. Similar to the embodiments with a constant curvature, the curvature of the curved section with a straight segment may be constant or it may follow previously mentioned shapes.

Figure 13:
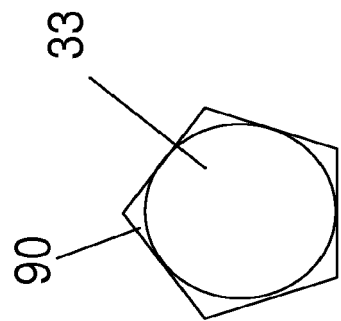
FIGS. 11-13 illustrate transverse cross-sectional views of various embodiments of wire distal tips about which springs are wrapped.
Figure 12:
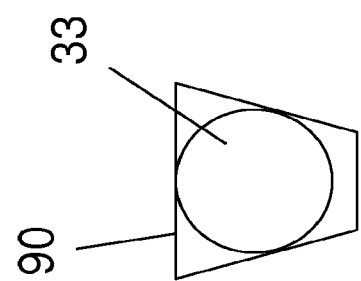
Figure 11:
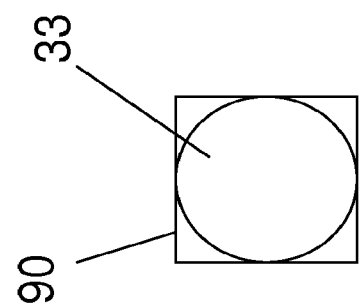

A spring 90 may be attached from the distal end 58 of the wire 33 along the first portion 54 and/or the second portion 56 to create an aggressive cutting surface. The ends of the spring may be brazed at multiple points. The spring 90 may follow the various profiles mentioned earlier. FIGS. 11-13 illustrate cross-sectional views of a spring following screw flights of a square, a trapezoid, and a pentagon, respectively.

The sharp corners of the various profiles (for example, a square, a triangle, a parallelogram, a pentagon) may dig into the blood vessel wall and ablate the vessel wall. The wire 33 may have a hemispheric or a flat free end depending on the intended use. The hemispheric end or flat free end may also be textured or roughened.

Figure 14:
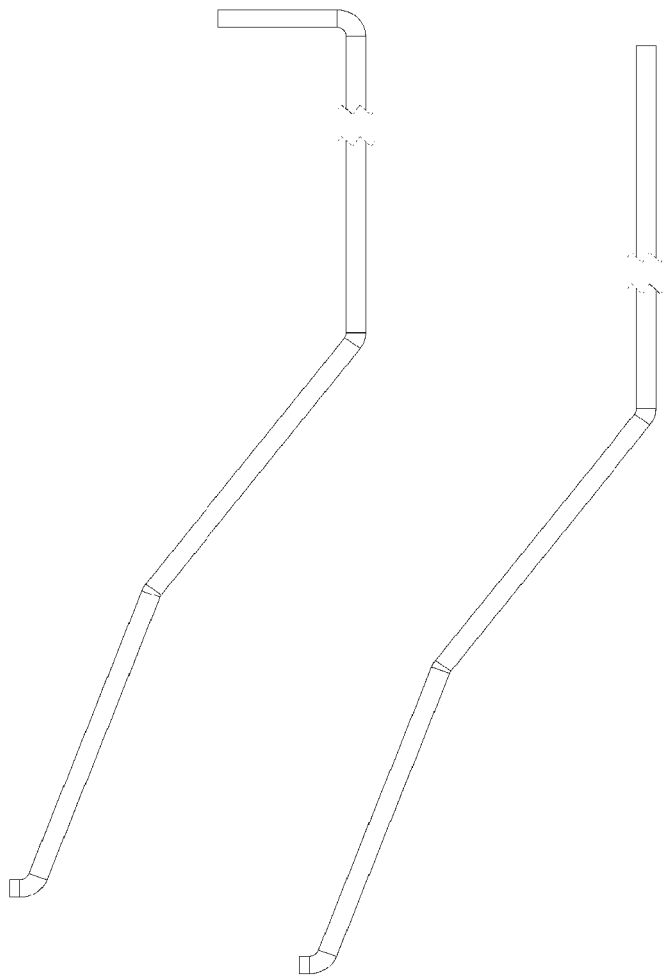

FIGS. 14-14A show a wire similar to that shown in FIG. 9 having first, second, and third linear segments distal to the main shaft.

Figure 15:
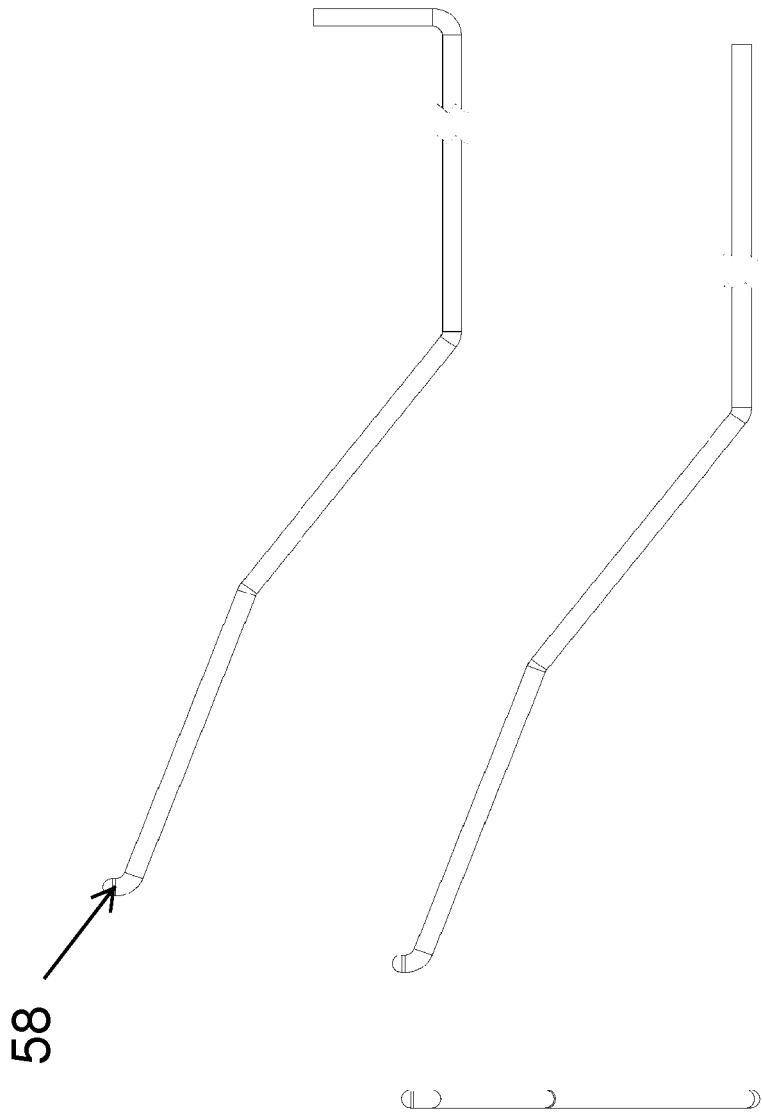
Figure 15A:

FIGS. 15-15A show a wire similar to that shown in FIGS. 14-14A, in which the free end of the third segment is hemispherical.

Figure 16:
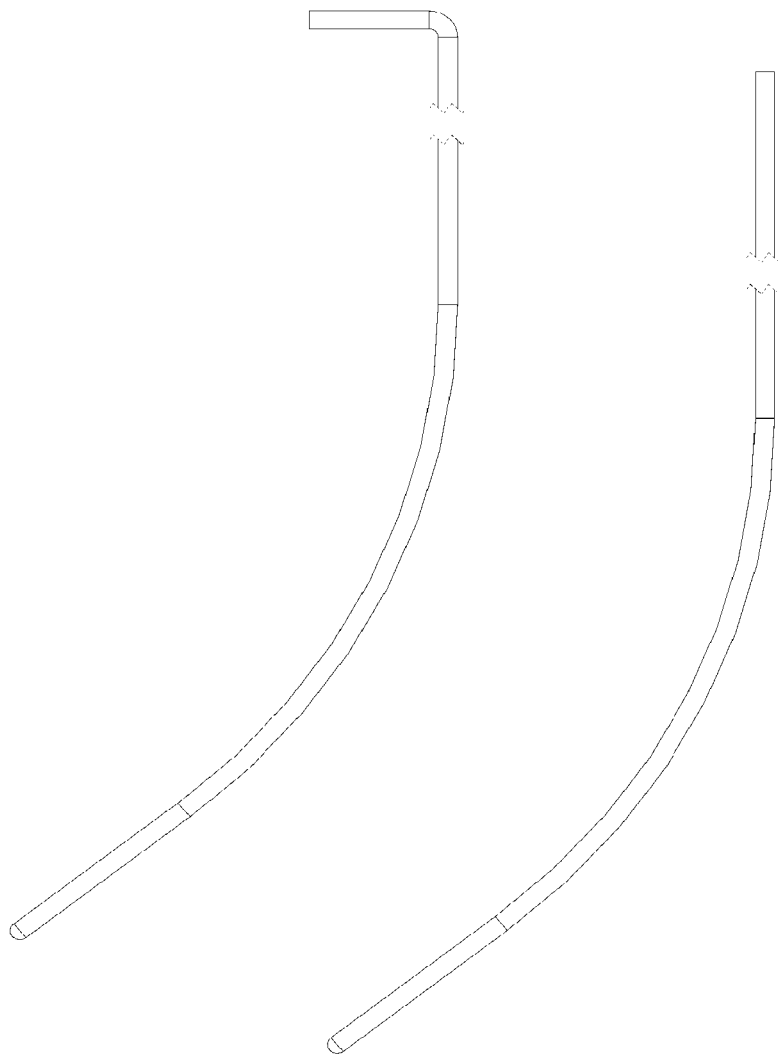

FIGS. 16-16A show a wire having a curved segment distal to the main shaft, and in which the free end of the curved segment is hemispherical.

Figure 17:
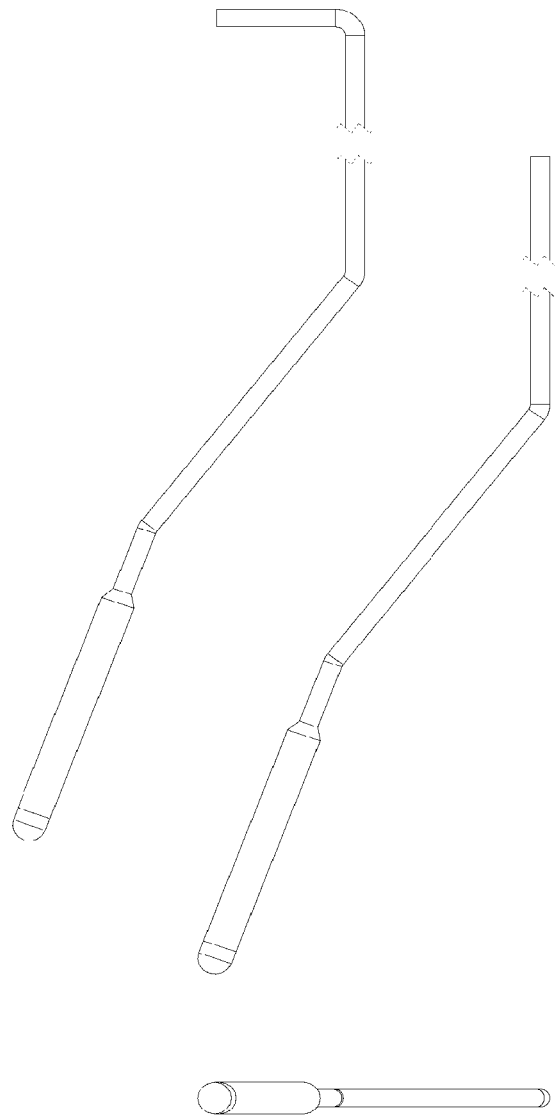

FIGS. 17-17A show a wire similar to that shown in FIG. 10 having first, second, and third linear segments, with weight added at the distal tip.

FIGS. 18-18A show a wire having a single linear segment distal to the main shaft, in which the linear segment terminates with a ball-shaped free end.

Figure 19:
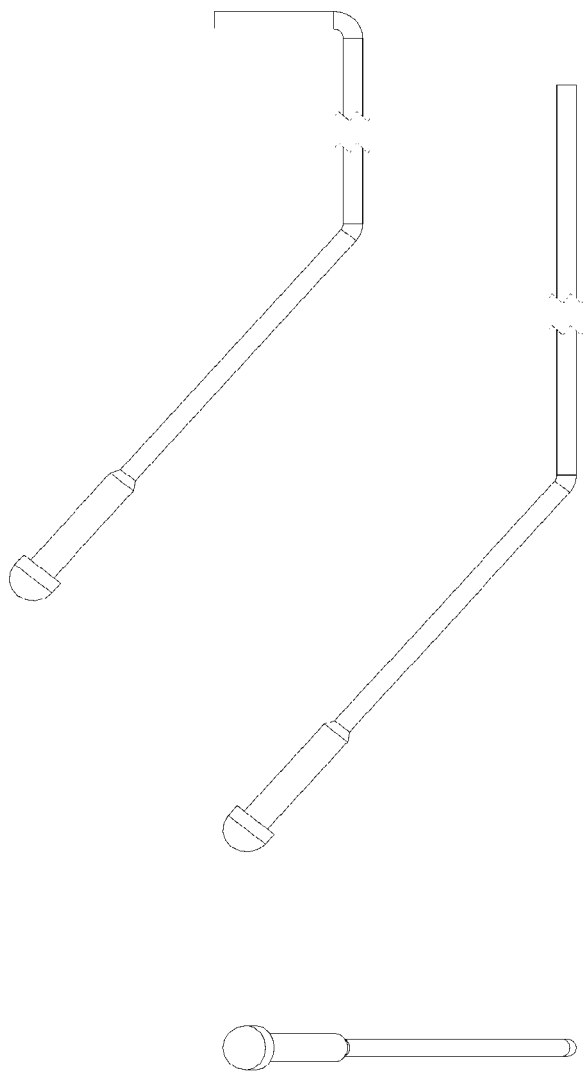

FIGS. 19-19A show a wire having a single linear segment distal to the main shaft, in which the distal tip has added weight and the free end is hemispherical.

Figure 20:
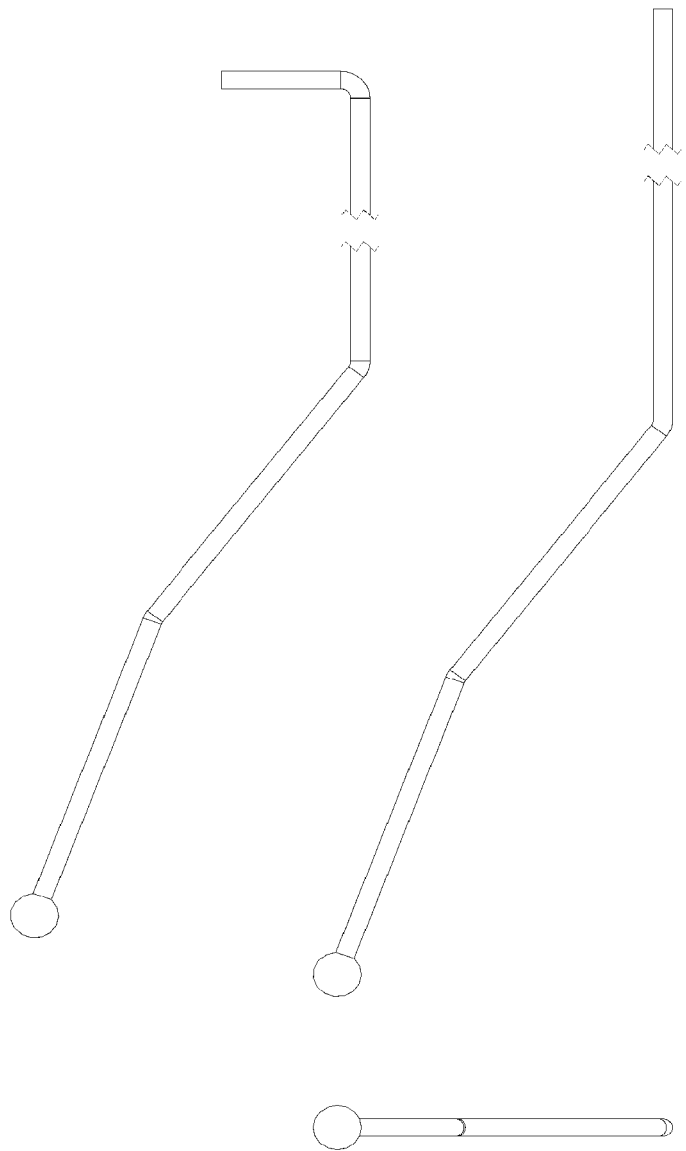

FIGS. 20-20A show a wire having two linear segments distal to the main shaft, in which the second linear segment terminates with a ball-shaped free end.

FIGS. 21-21A show a wire having two linear segments distal to the main shaft, in which the second linear segment has added weight and terminates with hemispherical free end.

Figure 22:
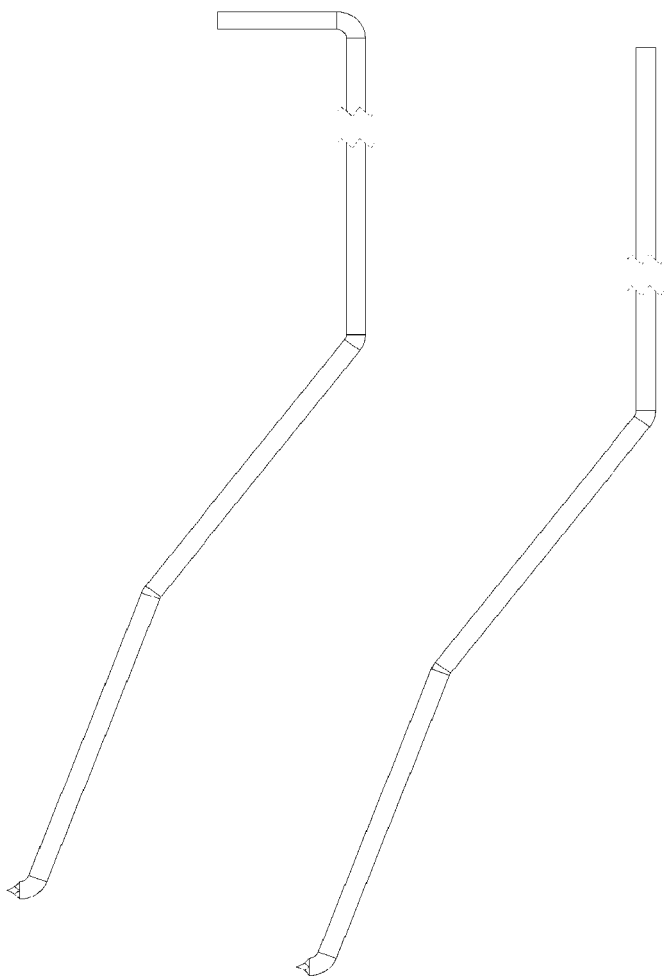
Figure 22A:

FIGS. 22-22A show a wire similar to that shown in FIGS. 14-14A, having three linear segments in which the third segment terminates with a sharp free end.

Figure 23:
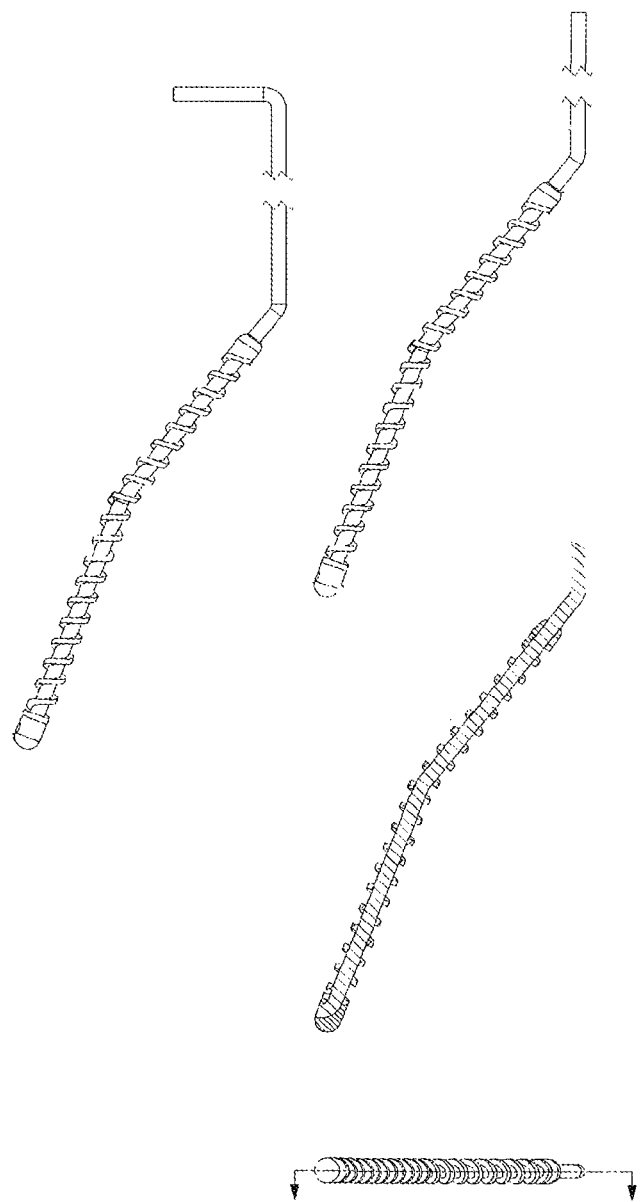
Figure 24:
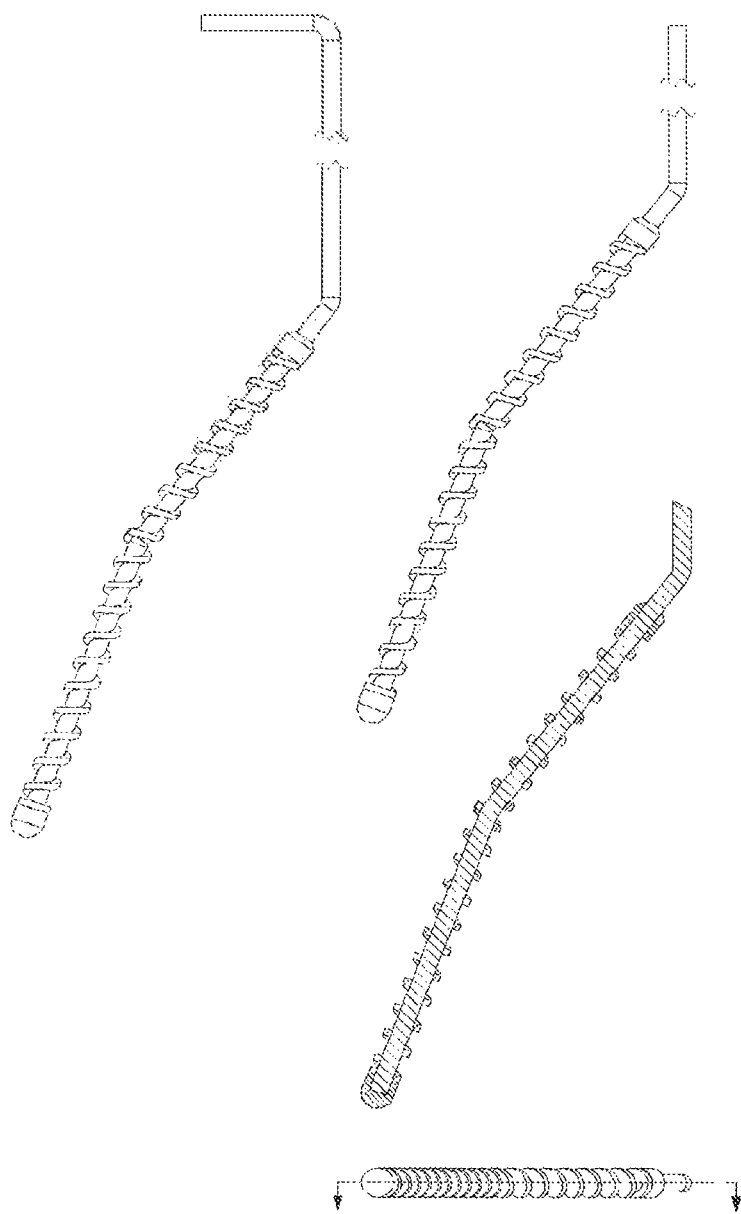

FIGS. 23-24 show wires having a spring wrapped around the distal portion of the wire.

What is claimed is:

1. A wire for use with a vascular treatment device, the wire comprising: a shaft having a proximal end and a distal end, the shaft further comprising: a first segment that extends from the proximal end to a bend, the first segment having a first diameter; and a second segment that extends from the bend to the distal end, the second segment including a first portion, a second portion, and a third portion, the first portion disposed between the bend and the second portion, the second portion disposed distal to the first portion, the second portion comprising a second diameter disposed at its distal end that is greater than the first diameter, the second diameter being a maximum diameter of the second portion, the third portion disposed distal to the second portion and defining a distal tip, the third portion having a third diameter that is greater than the second diameter, the first segment and the second segment being biased relative to each other at a first interior angle that is less than 180 degrees, the first portion and the second portion being biased relative to each other at a second interior angle that is less than 180 degrees, wherein the second interior angle is greater than the first interior angle, the second and third portions being axially offset from the proximal end, and at least a portion of the wire being configured to rotate within the vascular treatment device.

2. The wire of claim 1, wherein the distal end comprises a rounded distal tip.

3. The wire of claim 2, wherein the third portion comprises a textured surface.

4. The wire of claim 2, wherein the third portion comprises a hemispherical-shaped distal tip.

5. The wire of claim 4, further comprising a sleeve extending from the hemispherical-shaped distal tip towards the proximal end along the second portion of the wire, the sleeve adding strength to the hemispherical-shaped distal tip thereby increasing contact surface area to prevent detachment of the hemispheric-shaped distal tip.

6. The wire of claim 1, wherein the first interior angle is less than 140 degrees.

7. The wire of claim 1, wherein at least part of the second segment is weighted.

8. The wire of claim 7, wherein at least part of the second segment is eccentrically weighted relative to the first segment.

9. The wire of claim 1, wherein at least part of the second segment has a roughened surface.

10. The wire of claim 1, wherein the wire further comprises a spring disposed along the entirety of the second portion.

11. The wire of claim 1, wherein the first segment extends along a first axis and a length measured along a second axis that is perpendicular to first axis between the first segment and the distal end of the shaft is less than 0.3 inches.

12. A vascular treatment device comprising the wire of claim 1 and a sheath, the sheath defining a lumen within which at least a portion of the wire is disposed, the second diameter being less than an inner diameter of the sheath.

* * * * *

UNITED STATES PATENT AND TRADEMARK OFFICE
CERTIFICATE OF CORRECTION

PATENT NO. : 10,463,388 B2
APPLICATION NO. : 14/947256
DATED : November 5, 2019
INVENTOR(S) : Michael G. Tal Page 1 of 1

It is certified that error appears in the above-identified patent and that said Letters Patent is hereby corrected as shown below:

In the Claims

Column 10, Line 2 reads, "… of the hemispheric-shaped …" which should read, "… of the hemispherical-shaped …"

Column 10, Line 17 reads, "… that is perpendicular to first axis …" which should read, "… that is perpendicular to the first axis …"

Signed and Sealed this
Eleventh Day of February, 2020

Andrei Iancu
*Director of the United States Patent and Trademark Office*